US007963283B2

(12) United States Patent
Sinderby

(10) Patent No.: US 7,963,283 B2
(45) Date of Patent: Jun. 21, 2011

(54) MYOELECTRICALLY ACTIVATED RESPIRATORY LEAK SEALING

(75) Inventor: Christer Sinderby, Toronto (CA)

(73) Assignee: Universite de Montreal, Montreal (CA)

( * ) Notice: Subject to any disclaimer, the term of this patent is extended or adjusted under 35 U.S.C. 154(b) by 1259 days.

(21) Appl. No.: 10/466,699

(22) PCT Filed: Jan. 16, 2002

(86) PCT No.: PCT/CA02/00056
§ 371 (c)(1),
(2), (4) Date: Jul. 30, 2004

(87) PCT Pub. No.: WO02/056818
PCT Pub. Date: Jul. 25, 2002

(65) Prior Publication Data
US 2005/0011519 A1 Jan. 20, 2005

(51) Int. Cl.
*A61M 16/00* (2006.01)
(52) U.S. Cl. ......... 128/204.23; 128/204.18; 128/204.22; 128/205.25; 128/206.21; 128/206.24; 128/206.28; 128/207.12; 128/204.21; 600/546; 600/593; 600/587; 600/547
(58) Field of Classification Search ............. 128/204.23, 128/200.24, 204.18, 204.21, 204.26, 205.14, 128/205.16, 205.25, 206.21; 600/546, 593, 600/587, 547
See application file for complete search history.

(56) References Cited

U.S. PATENT DOCUMENTS

| | | | | |
|---|---|---|---|---|
| 4,471,775 A | * | 9/1984 | Clair et al. | 128/205.24 |
| 4,825,862 A | * | 5/1989 | Sato et al. | 128/207.15 |
| 4,915,103 A | * | 4/1990 | Visveshwara et al. | 128/204.23 |
| 4,924,862 A | * | 5/1990 | Levinson | 128/207.16 |
| 5,235,973 A | * | 8/1993 | Levinson | 128/207.15 |
| 5,452,715 A | | 9/1995 | Boussignac | |
| 5,820,560 A | | 10/1998 | Sinderby et al. | |
| 6,006,755 A | * | 12/1999 | Edwards | 128/898 |
| 6,102,041 A | * | 8/2000 | Boussignac et al. | 128/207.15 |
| 6,588,423 B1 | * | 7/2003 | Sinderby | 128/204.23 |
| 2003/0188748 A1 | * | 10/2003 | Sinderby et al. | 128/204.21 |

FOREIGN PATENT DOCUMENTS

JP S54/037397 3/1979

(Continued)

*Primary Examiner* — Steven O Douglas
*Assistant Examiner* — Clinton Ostrup
(74) *Attorney, Agent, or Firm* — Fay Kaplun & Marcin, LLP

(57) ABSTRACT

The method and system are for sealing/unsealing (regulating) airway leaks occurring between the ventilator circuit and respiratory airways during lung ventilatory support in response to myoelectrical activity of diaphragm. Myoelectrical activity of a patient's respiratory-related muscle is sensed to detect respiratory effort, and to produce a myoelectrical signal representative of the sensed muscle myoelectrical activity. Respiratory flow and pressure can also be measured to produce respective respiratory pressure and respiratory flow signals. A logic trigger sealing/unsealing of airway leaks in relation to the myoelectrical signal, respiratory flow signal and/or respiratory pressure signal to assist respiration of the patient. The amplitude of the myoelectrical signal is compared to a given threshold, and airway leaks are sealed when the amplitude of the myoelectrical signal is higher than this threshold. Increment of myoelectrical signal amplitude can be also detected to trigger the airway leak regulating device to seal the airway leaks, while decrement of the myoelectrical signal amplitude can be detected to unseal the airway leaks and thus permit air evacuation from the patient's lungs.

35 Claims, 12 Drawing Sheets

FOREIGN PATENT DOCUMENTS

| | | |
|---|---|---|
| JP | S62-186872 | 8/1987 |
| JP | 2-159282 | 6/1990 |
| JP | 7-88186 | 4/1995 |
| JP | 2001-523127 | 11/2001 |
| JP | 2002-0504405 | 2/2002 |
| WO | WO 99 33508 | 7/1999 |
| WO | 99/43374 | 9/1999 |
| WO | WO 9943374 A1 * | 9/1999 |
| WO | WO 9962580 A1 * | 12/1999 |
| WO | WO 00 37135 | 6/2000 |
| WO | WO 01 00267 | 1/2001 |
| WO | 01/08735 | 2/2001 |
| WO | 01/19439 | 3/2001 |
| WO | 01/19440 | 3/2001 |

* cited by examiner

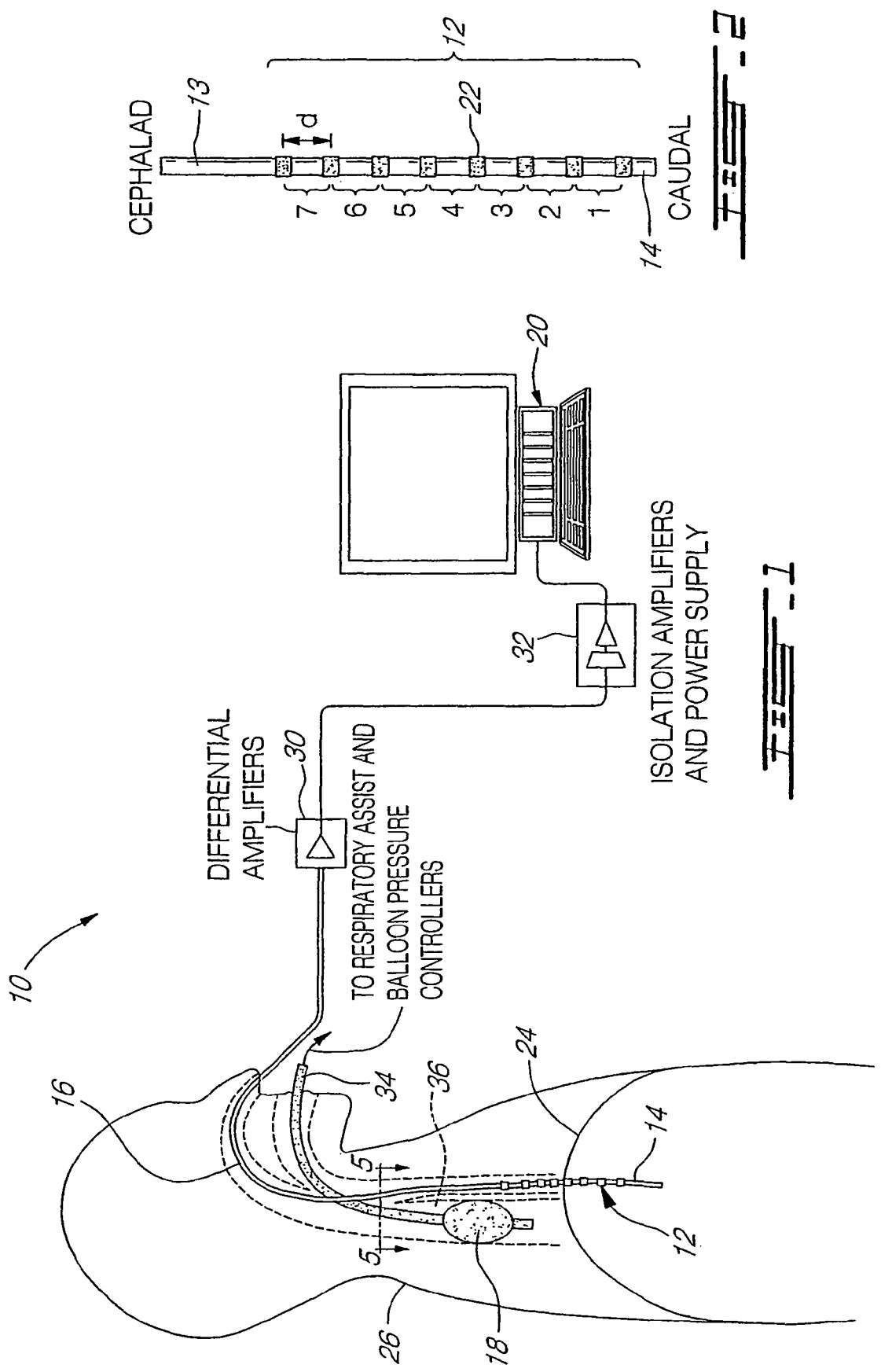

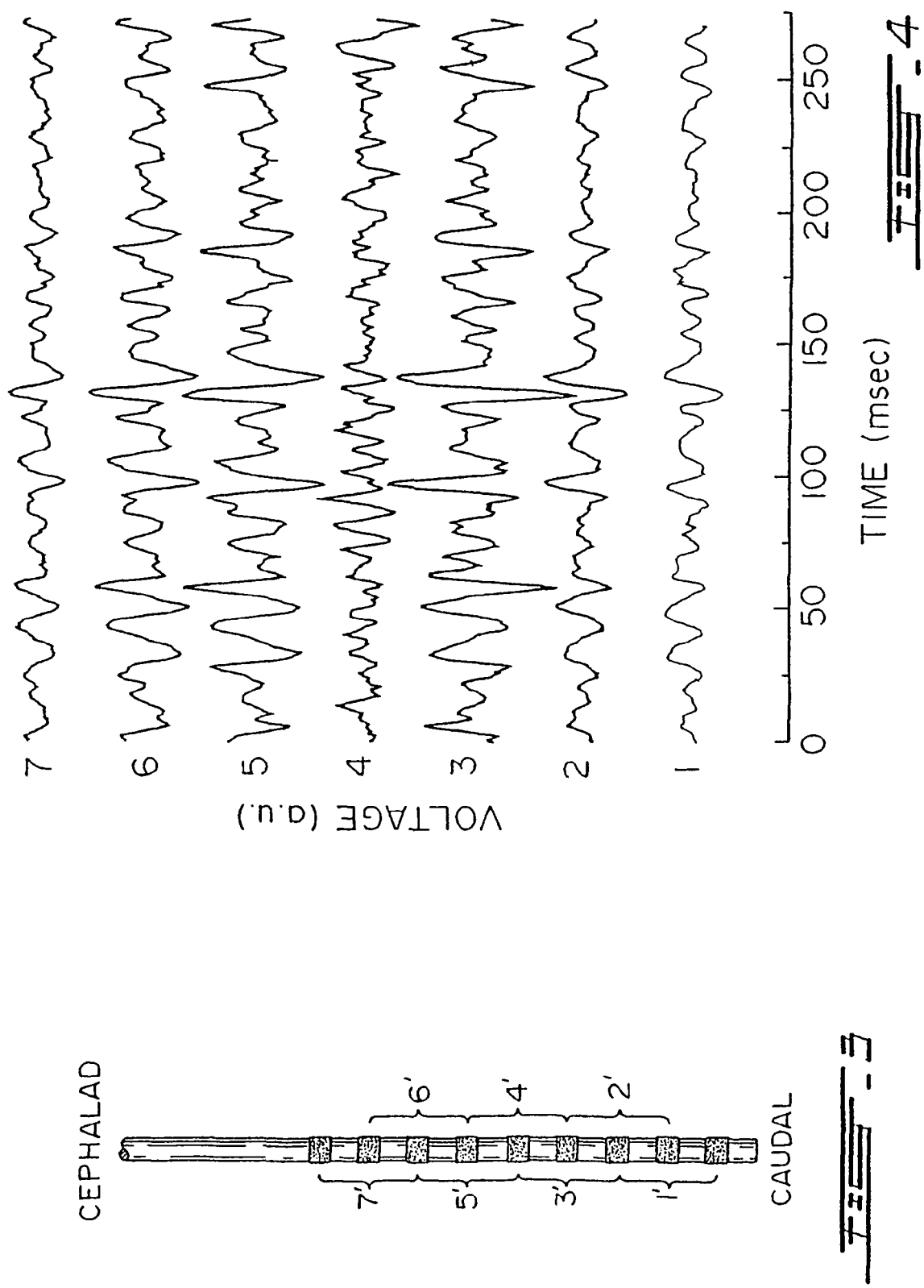

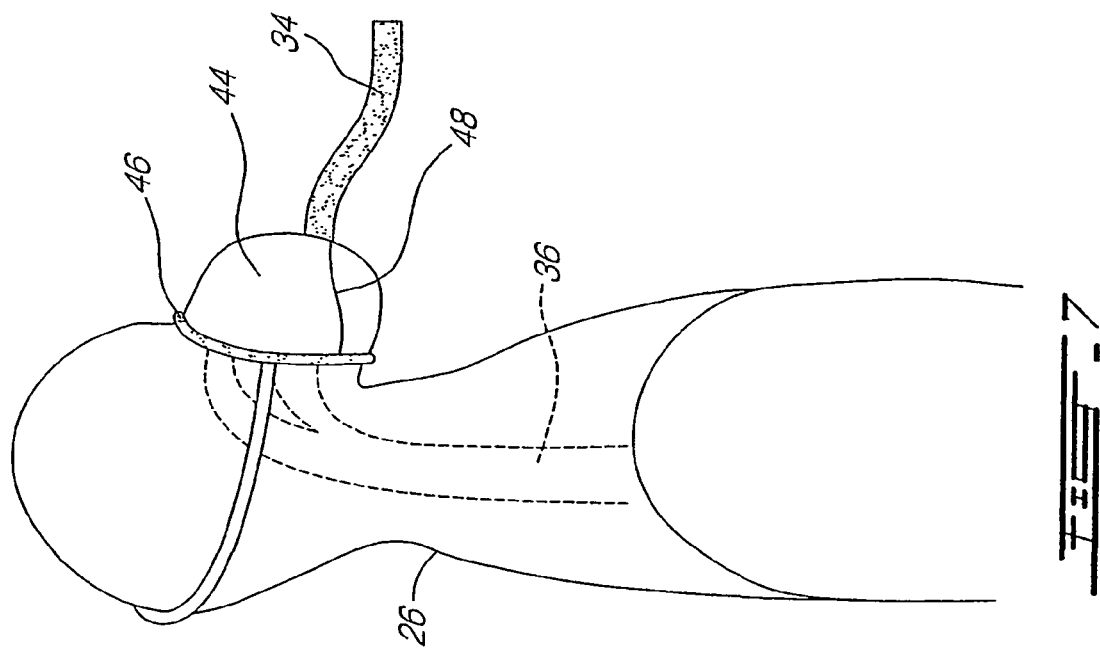
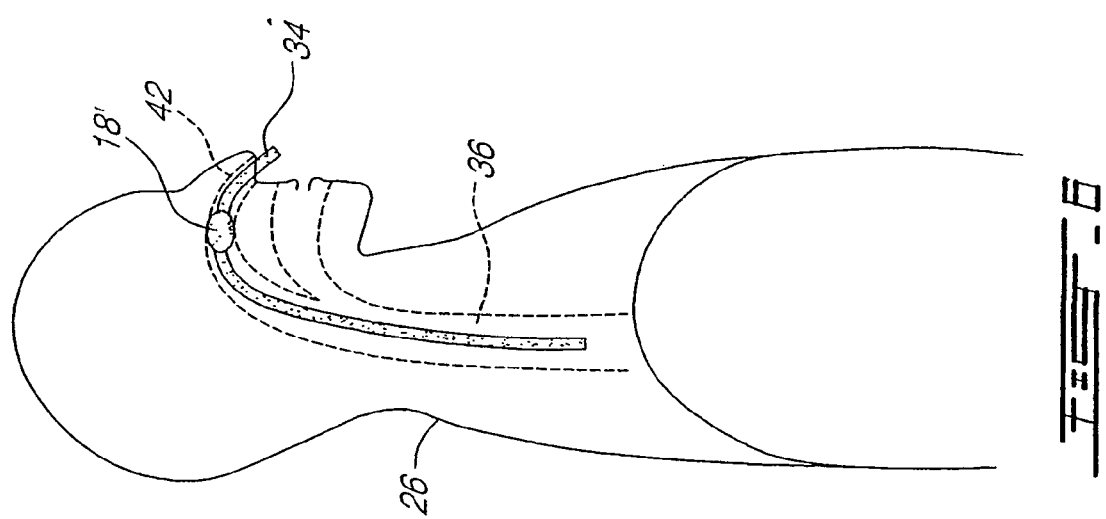
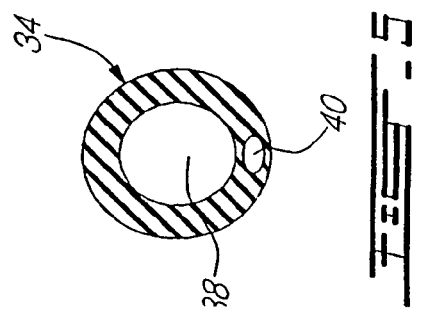

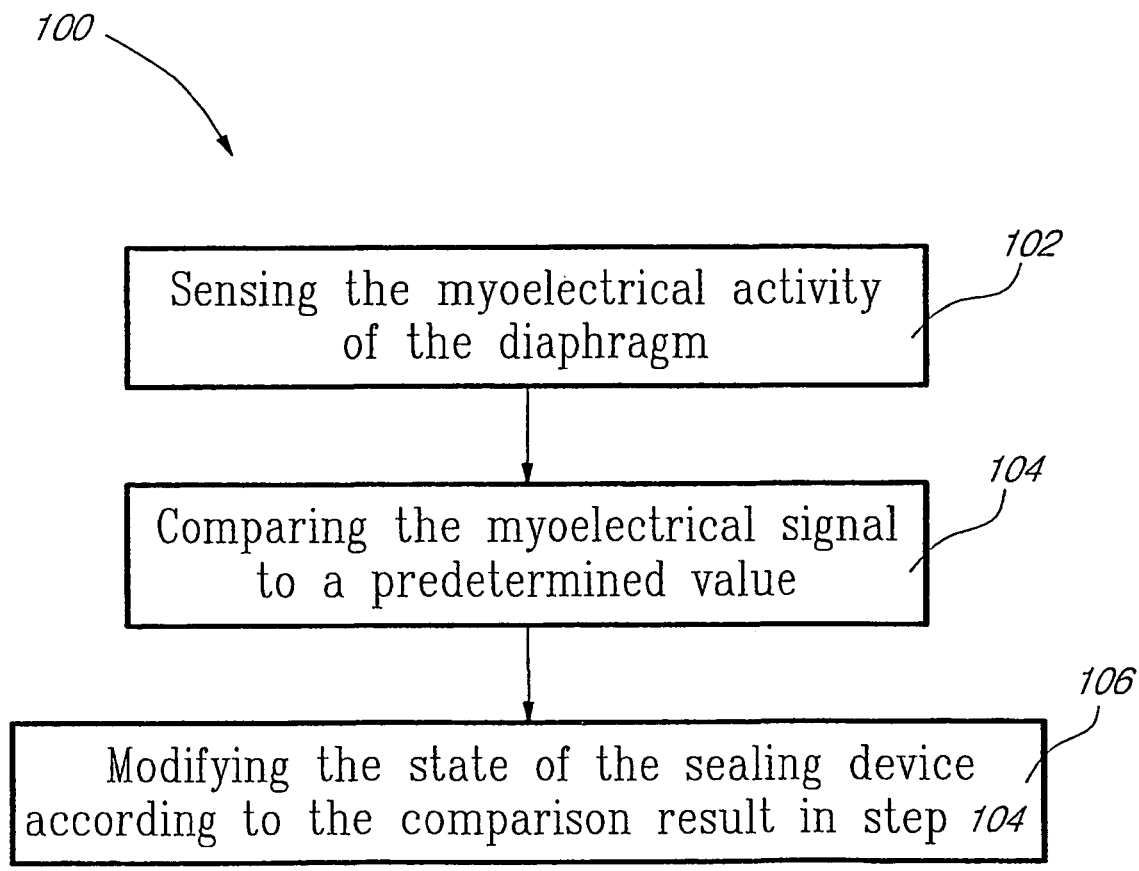

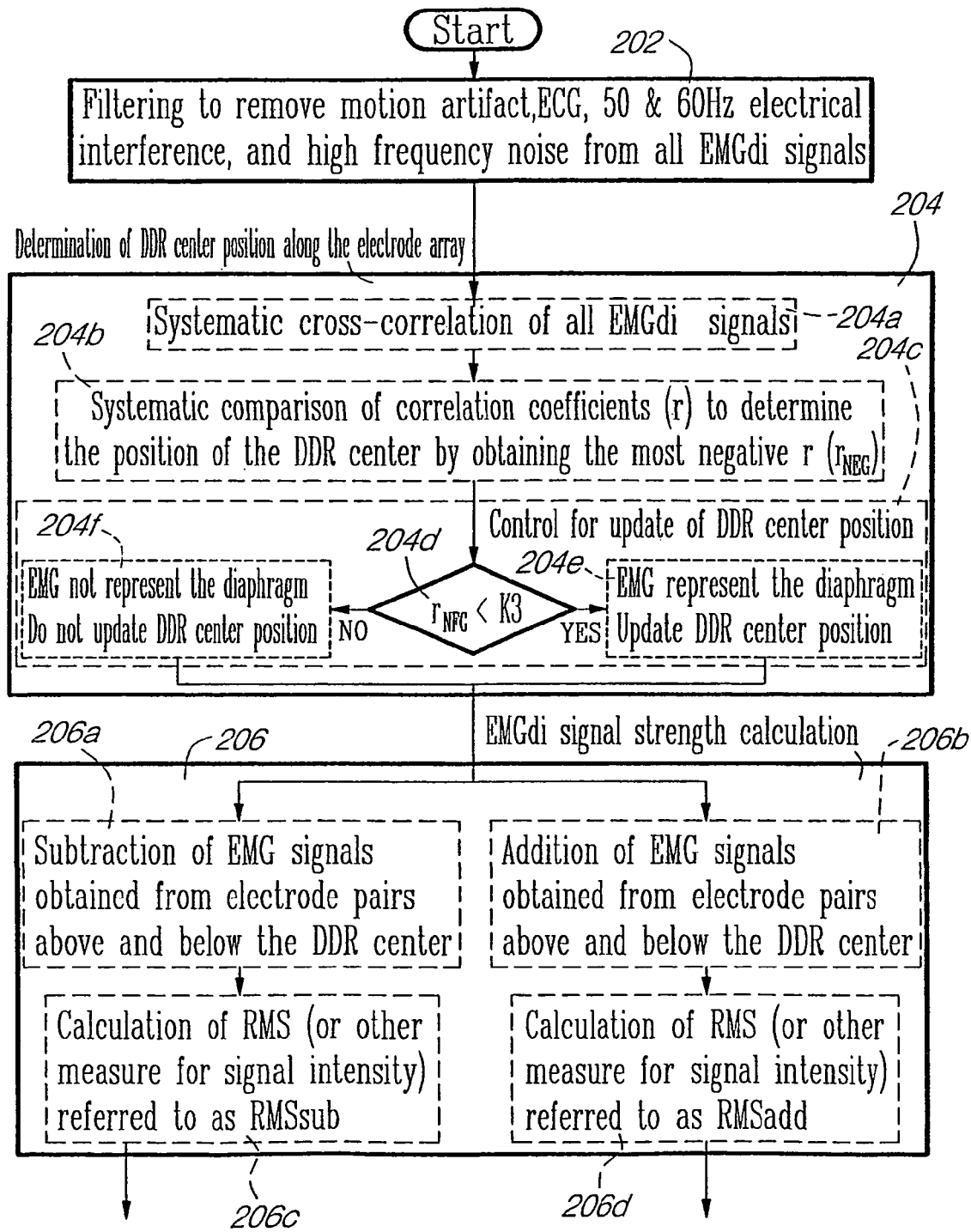

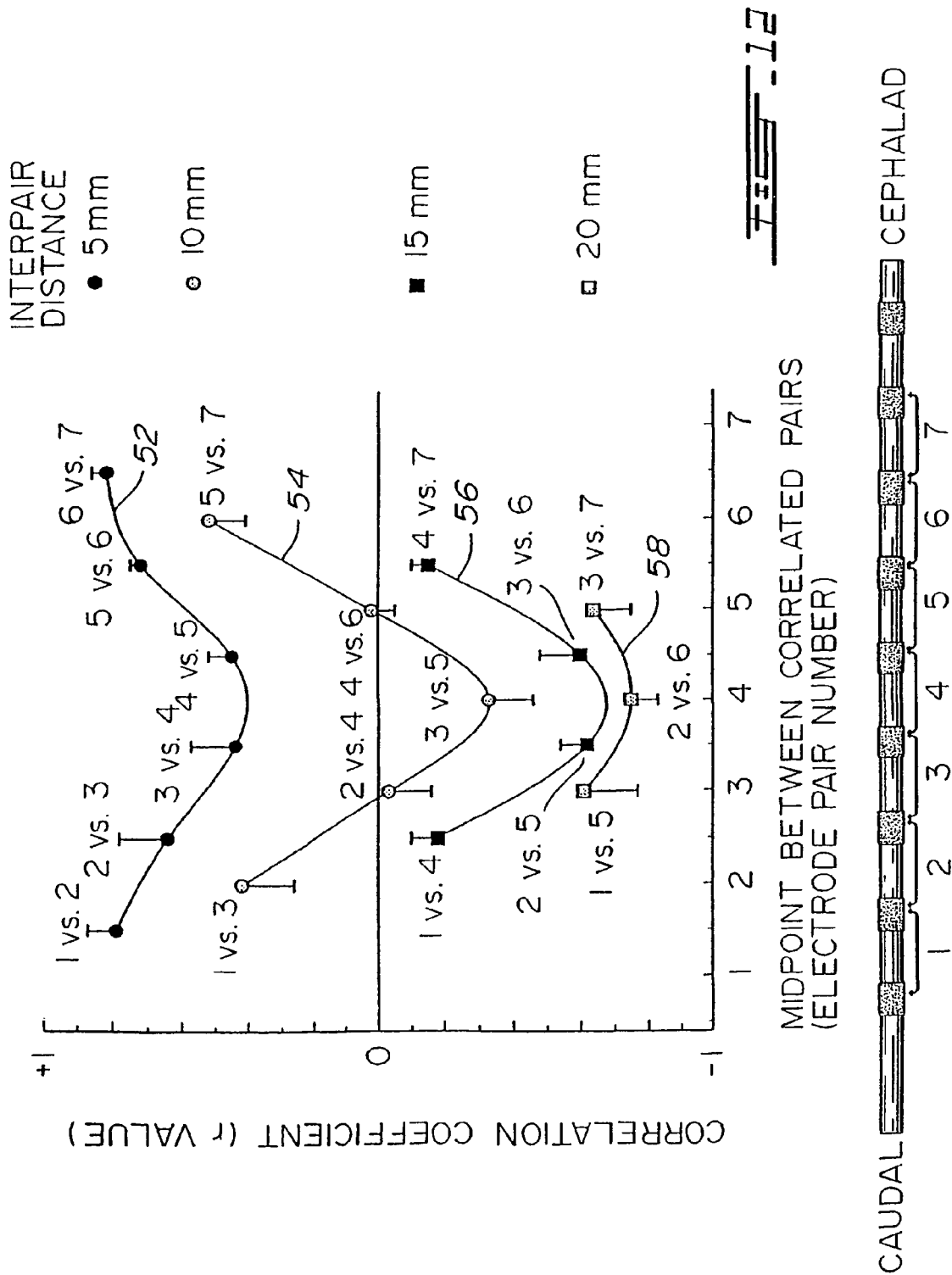

MYOELECTRICALLY ACTIVATED RESPIRATORY LEAK SEALING

FIELD OF THE INVENTION

The present invention relates to ventilatory support systems. More particularly, the present invention is concerned with a myoelectrically activated respiratory leak sealing method and system.

BACKGROUND OF THE INVENTION

Inherent to methods of administrating ventilatory support via delivering inspiratory flow, volume, and/or pressure to the airways is the influence of airway leaks occurring between the ventilator circuit and respiratory airways. A poor seal between the device used for administration of ventilatory support (e.g., endotracheal tube, face/nasal mask) and the patient (e.g., airway, airway opening) introduces difficulties to deliver appropriate gas flow, volume, or pressure into the airway system in order to inflate the lungs.

OBJECTS OF THE INVENTION

An object of the present invention is to use myoelectrical activity of the diaphragm or other respiratory-related muscles to activate and/or to deactivate a seal in order to regulate leaks between the ventilator circuit and respiratory airways.

SUMMARY OF THE INVENTION

A present invention relates to a method and system for sealing/unsealing airway leaks between the patient's airways and a ventilatory support apparatus in response to a respiratory effort via the use of myoelectrical activity of the diaphragm (or other muscles associated with respiratory effort).

Methods and systems according to the present invention allow synchronizing the activation of the seal between the respiratory airways and ventilator circuit with the neural activation of inspiratory muscles.

Methods and systems according to the present invention further allow to reduce the problems related to the interface and the leaks occurring between the respiratory airways and ventilator circuit during the entire (or parts of) the period of neural inspiratory activation, which help to ensure adequate delivery of gas flow, volume and/or pressure into the lungs.

Methods and systems according to the present invention also allow synchronizing the deactivation of the seal between the respiratory airways and ventilator circuit with the neural deactivation of inspiratory muscles.

More specifically, according to the present invention, there is provided a method for controlling an air seal between a ventilator air circuit and a patient's respiratory airways, comprising:

sensing myoelectrical activity of a respiratory-related muscle of the patient so as to yield at least one myoelectrical signal representative of respiratory effort of the patient;

comparing the at least one myoelectrical signal to a predetermined value, so as to determine the highest value therebetween; and modifying the seal according to the highest value so as to control the leak.

According to another aspect of the present invention, there is provided a system for controlling an air seal between a ventilator air circuit and a patient's respiratory airways, comprising:

a controller;

a myoelectrical sensor connected to the controller, the sensor being configured to sense at least one myoelectrical signal representative of the respiratory effort of the patient; and a respiratory sealing device connected to the controller and configured to modify the air seal according to the at least one sensed myoelectrical signal.

According to still another aspect of the present invention, there is provided a system for controlling an air seal between a ventilator air circuit and a patient's respiratory airways, comprising:

means for sensing myoelectrical activity of a respiratory-related muscle of the patient;

means for modifying the air seal; and means for controlling the air seal modifying means depending on the sensed myoelectrical activity.

Other objects, advantages and features of the present invention will become more apparent upon reading the following non-restrictive description of preferred embodiments thereof, given by way of example only with reference to the accompanying drawings.

BRIEF DESCRIPTION OF THE DRAWINGS

In the appended drawings:

FIG. 1 is a schematic view of a myoelectrically activated respiratory leak-sealing system, according to a first embodiment of the present invention, illustrated on a human patient;

FIG. 2 is a front elevational view of the myoelectrical sensor of FIG. 1, according to a first embodiment of the present invention;

FIG. 3 is a front elevational view of the myoelectrical sensor of FIG. 1, according to a second embodiment of the present invention;

FIG. 4 is a graph showing a set of EMG signals of the diaphragm (EMGdi signals) detected by pairs of successive electrodes of the sensor of FIG. 2;

FIG. 5 is a cross-sectional view taken along line 5-5 of FIG. 1;

FIG. 6 is a schematic view of a respiratory sealing device, according to a second embodiment of the present invention, illustrated inserted in a nasal air passage of the patient of FIG. 1;

FIG. 7 is a schematic view of respiratory sealing device according to a third embodiment of the present invention, illustrated mounted on the face of the patient of FIG. 1;

FIG. 8 is a flow chart of a myoelectrically activated respiratory leaksealing method according to an embodiment of, the present invention;

FIGS. 9a and 9b illustrate a flow chart of step 102 from FIG. 8;

FIG. 12 is a graph showing the distribution of correlation coefficients calculated for determining the position of the centre of the depolarizing region of the diaphragm along the array of electrodes of FIG. 2;

DESCRIPTION OF THE PREFERRED EMBODIMENT

Figure 9B:
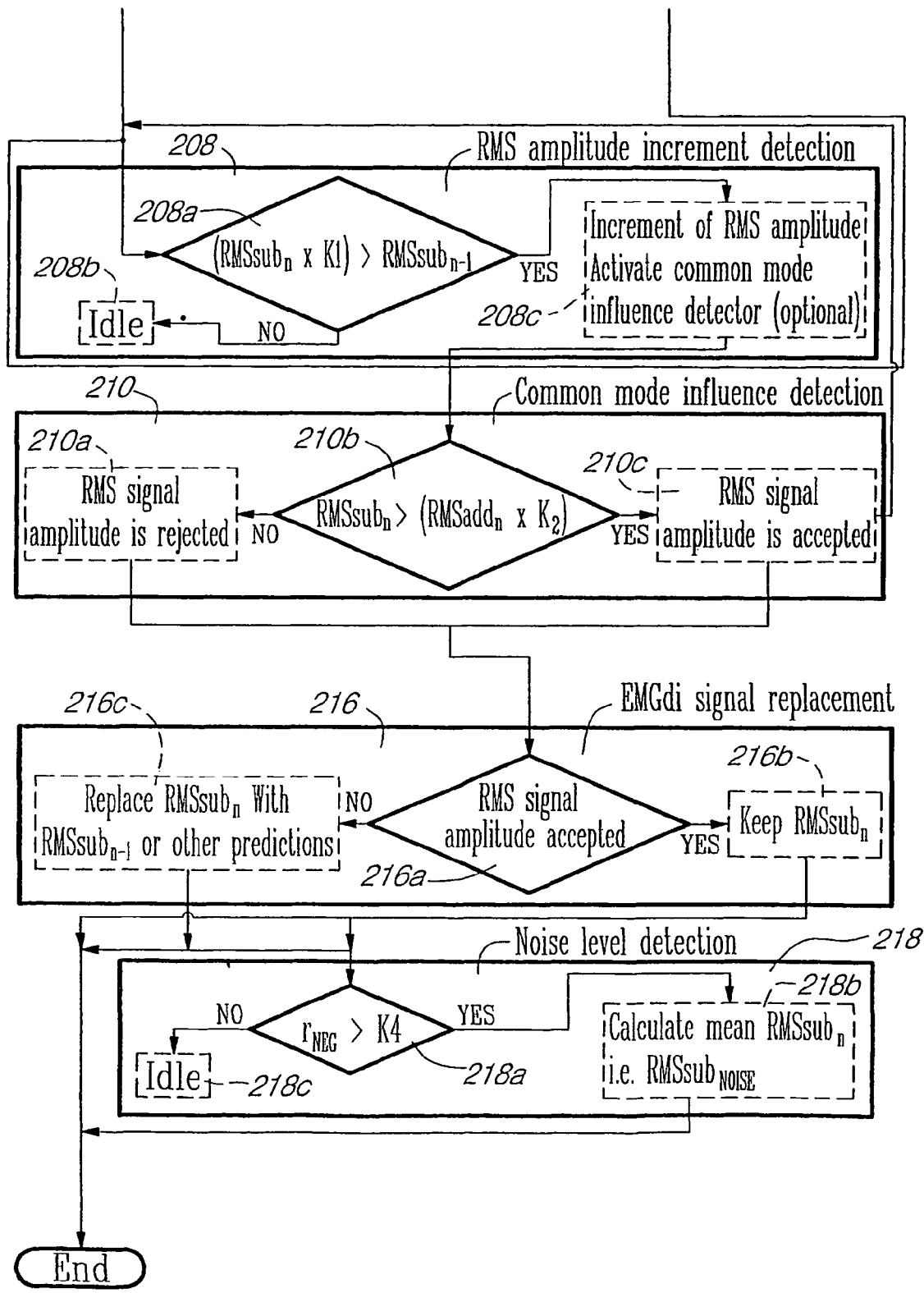

Turning to FIG. 1 of the appended drawings, a myoelectrically activated respiratory leak sealing system 10 according to a first embodiment of the present invention is illustrated.

The system 10 comprises a myoelectrical sensor 12 mounted on the free end section 14 of an oesophageal catheter 16, a respiratory sealing device in the form of a sealing balloon 18, and a controller 20.

As illustrated in FIG. 2, the myoelectrical sensor 12 is in the form of an array of electrodes 22 provided with a constant inter-electrode distance d, and allows measuring the electromyographic (EMG) activity of the diaphragm 24 (EMGdi) of a patient 26.

The electrodes 22 are mounted on the free end section 14 of the catheter 16 by winding stainless steel wire (not shown) around the catheter 16. The wound stainless steel wire presents a rough surface smoothed out by solder, which in turn is electroplated with nickel, copper and then gold or silver. Of course, it is within the scope of the present invention to use other electrode structures.

In the embodiment illustrated in FIGS. 1 and 2, the free end section 14 of the catheter 16 is provided with an array of eight electrodes 22 defining seven pairs 1, 2, 3, 4, 5, 6 and 7 of successive electrodes 22 respectively collecting seven different EMGdi signals.

Although it has been found that EMG activity of the diaphragm (EMGdi) can be measured accurately with an oesophageal catheter 16 provided on the free end section 14 thereof with an array of eight electrodes 22, a different number and/or configuration of pairs of electrodes 22 can be contemplated depending on the patient's anatomy and movement of the diaphragm 24. Also, the pairs 1-7 do not need to be pairs of successive electrodes; FIG. 3 illustrates an array of nine electrodes to form seven overlapping pairs of electrodes 1'-7'.

Alternatively, the electrodes 22 can possibly be applied to a nasogastric tube (not shown), which is routinely introduced in intensive-care unit (ICU) patients.

Electric wires (not shown) interconnect each pair of successive electrodes such as 1-7 (FIG. 2) with a respective one of a group of differential amplifiers 30 (FIG. 1). Obviously, these electric wires follow the catheter 16 from the respective electrodes 22 to the corresponding amplifiers 30, and are preferably integrated to the catheter 16.

The electric wires transmitting the EMGdi signals collected by the various pairs 1-7 of electrodes 22 are shielded to reduce the influence of external noise, in particular disturbance from the 50 or 60 Hz current and voltage of the electrical mains.

The group of differential amplifiers 30 amplifies (first subtraction step of the double subtraction technique that will be described hereinbelow) and band-pass filters each EMGdi signal. This first subtraction step may also be carried out in the controller, which is in the form of a personal computer 20, when the amplifiers 16 are single-ended or equivalently designed amplifiers (monopolar readings).

A common problem in recording EMGdi signals is to maintain the noise level as low and as constant as possible. Since the electric wires transmitting the EMGdi signals from the electrodes 22 to the differential amplifiers 30 act as an antenna, these electric wires are shielded to thereby protect the EMGdi signals from additional artefactual noise. Also, the package enclosing the differential amplifiers 30 is preferably made as small as possible (miniaturized) and is positioned in close proximity to the patient's nose to decrease as much as possible the distance between the electrodes 22 and the amplifiers 30.

The personal computer 20 allows sampling the amplified EMGdi signals through respective isolation amplifiers of a unit 32, to form signal segments of fixed duration. Unit 32 supplies electric power to the various electronic components of the differential and isolation amplifiers while ensuring adequate isolation of the patient's body from such power supply. The unit 32 also incorporates bandpass filters included in the respective EMGdi signal channels to reduce the effects of aliasing. The successive EMGdi signal segments are then digitally processed into the personal computer 20 after analog-to-digital conversion thereof. An analog-to-digital converter implemented in the personal computer 20 conveniently carries out this analog-to-digital conversion.

It is believed to be within the capacity of those of ordinary skill in the art to construct suitable differential amplifiers 30 and adequate isolation amplifiers and power supply unit 32. Accordingly, the amplifiers 30 and the unit 32 will not be further described in the present specification.

As shown in FIG. 1, the catheter 16 is introduced into the patient's oesophagus through one nostril or the mouth until the array of electrodes 22 is situated at the level of the gastroesophageal junction. Since the diaphragm 24 and/or the oesophagus slightly moves during breathing of the patient 26, the array of electrodes 22 also slightly moves about the diaphragm 24. As will be explained in the following description, automatic compensation for this displacement is advantageously provided for.

An example of the seven EMGdi signal components (hereinafter EMGdi signals) collected by the pairs 1-7 of successive electrodes 22 (FIGS. 1 and 2) and supplied to the computer 20 is illustrated in FIG. 4.

The sealing balloon 18 (FIG. 1) is mounted on a ventilatory assist tube 34 thereabout.

The tube 34 is an endotracheal tube that is to be inserted in the trachea 36 of the patient 26 via the mouth or the nose or tracheotomy. The tube 34 is part of the ventilator air circuit of a conventional ventilatory assistance system and is therefore connected to ventilator assist and sealing balloon controllers (both not shown).

As shown in FIG. 5, the ventilator assist tube 34 comprises two lumens: a ventilator assist lumen 38 and a seal pressure control lumen 40. The ventilatory assist lumen 48 is an air passage from the ventilator assist device (not shown) and the patient's lungs. The seal pressure control lumen 40 is an air or fluid passage from a balloon inflation device (not shown) to the sealing balloon 18 or mask 46 (see FIG. 7). The balloon inflation device can be any device providing a known volume or a known pressure.

The sealing balloon controller is connected to the computer 20 and its operation is controlled thereby.

In operation, the ventilatory endotracheal ventilatory assist tube 34, with the sealing balloon 18 integrally mounted thereto, are inserted in the trachea 36 of the patient 26 via the mouth or the nose or tracheotomy. The oesophageal catheter 16 with the myoelectrical sensor 12 are introduced into the patient's oesophagus through one nostril or mouth until the array of electrodes 22 is located at the level of the gastroesophageal junction.

As will be explained in further detail hereinbelow, upon inspiration of the patient 26, the change in EMG activity of the diaphragm 24 is detected by the sensor 12 and the detected signal is analysed by the computer 20 that commands the balloon controller to inflate the sealing balloon 18, thereby providing an air seal between the ventilatory assist tube 34 and the patient's respiratory airways (the trachea 36 in this exemplary embodiment). Upon expiration of the patient 26, the sensor 12 detects the change in EMG activity of the diaphragm 24 and the computer 20 commands the balloon controller to deflate the balloon 18, thereby allowing gas leaks around the ventilatory assist tube 34.

FIGS. 6 and 7 show two alternative embodiments of respiratory sealing devices.

In the embodiment of FIG. 6, the sealing balloon 18' is so mounted to the ventilatory assist tube 34 as to be located, in operation, in the nasal passage 42 of the patient 26. In operation, upon inspiration of the patient 26, the sealing balloon 18' inflates, thereby providing an air seal between the ventilatory assist tube 34 and the patient's respiratory airways (the nasal passage 42 in this exemplary embodiment). Upon expiration of the patient 26, the sealing balloon 18' will deflate, thereby allowing gas leaks around the ventilatory assist tube 34, and also giving the patient 26 the ability to speak.

FIG. 7 shows the human patient 26 with a ventilatory assist facemask 44 over its mouth and nose. The facemask 44 is connected to the ventilatory assist tube 34. The ventilator assist tube 34 is in turn connected to ventilator assist and sealing balloon controllers (both not shown). In this particular embodiment, a seal 46 is provided at the edge portion of facemask 44. The seal 46 is fluidly connected to a ventilator assist tube seal pressure control lumen 40 (FIG. 5) through the facemask seal pressure control lumen 48. Upon inspiration of the patient 26, the seal 46 inflates, thereby providing an air seal between the facemask 44 and the patient's respiratory airways (the patient's mouth and nose in this exemplary embodiment). Upon expiration of the patient 26, the seal 46 deflates, thereby allowing gas leaks around the facemask 62.

Other features of the system 10 will become more apparent upon reading the following description of a myoelectrically activated respiratory leak sealing method 100, according to an embodiment of the present invention. As will now be described in more detail, the method 100 allows controlling the air seal 18.

Generally stated, the method 100 comprises the following steps:
  102—sensing the myoelectrical activity of the diaphragm 24;
  104—comparing the myoelectrical signal to a predetermined value; and
  106—modifying the state of the sealing device 18 according to the comparison result in step 104.

Each of these steps will now be described in further detail.

In step 102, the myoelectrical activity of the diaphragm is measured using sensor 12. The objective is to provide a myoelectrical signal representative of the respiratory effort of the patient 26.

More specifically, a crural diaphragm EMG is recorded from a sheet of muscle whose fibre direction is generally perpendicular to an oesophageal bipolar electrode. The region from which the action potentials are elicited, the electrically active region of the diaphragm (DDR), and the centre of this region, the DDR centre, may vary during voluntary contractions, in terms of their position with respect to an oesophageal electrode. Depending on the position of the bipolar electrode with respect to the DDR centre, the EMGdi signal is filtered to different degrees.

Based on experimental results and anatomical descriptions of the crural diaphragm, a transfer function for diaphragm EMG measured $$\text{Perpendicular filtering} \approx \frac{(K_0(\omega(h-d)/v) - K_0(\omega(h+d)/v))^2}{K_0^2(\omega a/v)}$$

with bipolar electrodes, such as electrodes 22, has been developed where, $K_0(\ )$=modified Bessel function, $\omega$=angular frequency (i.e. $2\pi f$ (f being the frequency), h=distance between the signal source and observation point, d=½ inter-electrode distance, v=conduction velocity, a=muscle fiber diameter.

Based on this transfer function, a signal analysis procedure has been developed which involves:
  (a) locating the electrode pair at the centre of the diaphragm depolarizing region (DDR) (this region will be defined hereinbelow);
  (b) selecting the signals above and below the centre of the DDR (reversed in polarity) yielding the highest signal-to-noise ratio; and
  (c) subtracting these two signals (double subtraction technique).

The double subtraction technique allows to reduce the influence of movement of the DDR centre relative to the electrode array 12 on the EMG power spectrum centre frequency and root mean square values, to increase the signal to noise ratio by 2 dB, and to increase the number of EMG samples that are accepted by the signal quality indices by 50%. A more detailed description of the above mentioned double subtraction technique is given hereinbelow.

Step 102 will now be described in further detail with reference to FIG. 9.

Figure 10A:
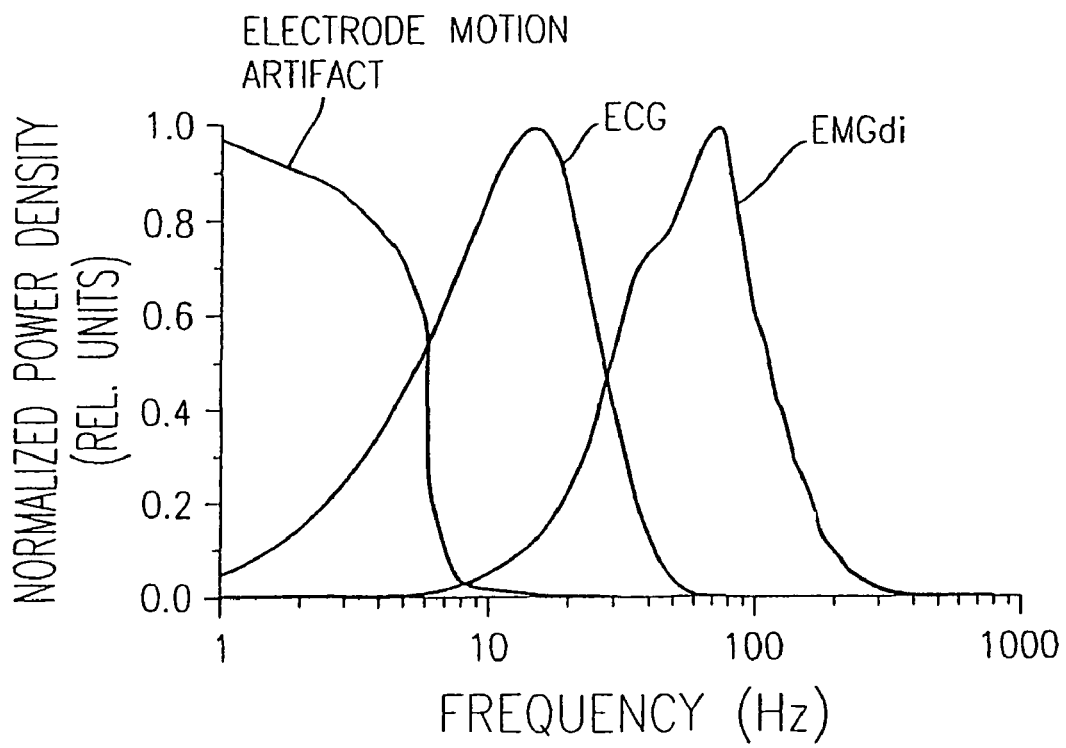
FIG. 10a is a graph showing the power density spectrum of electrode motion artefacts, the power density spectrum of electrocardiogram (ECG), and the power density spectrum of EMGdi signals.

The first operation (substep 202) performed by the computer 20 is a filtering operation to remove from all the EMGdi signals of FIG. 4 electrode motion artefacts, ECG, 50 and 60 Hz interference from the electrical network, and high frequency noise. The graph of FIG. 10a shows the power density spectrum of the above defined electrode motion artefacts, the power density spectrum of ECG, and the power density spectrum of EMGdi signals.

It is to be noted that motion artefacts are induced by motion of the electrodes 22. More generally, motion artefacts are defined as a low frequency fluctuation of the EMGdi signals' DC level induced by mechanical alterations of the electrode metal to electrolyte interface i.e. changes in electrode contact area and/or changes in pressure that the tissue exerts on the electrode.

The influence of ECG on the EMGdi signals can be suppressed or eliminated in different ways. Depending on the working mode, i.e. on-line or off-line analysis, time domain or frequency domain processing, different optimal signal conditioning methods can be chosen. In time-critical applications, an optimized filtering has been found advantageous.

Figure 10B:
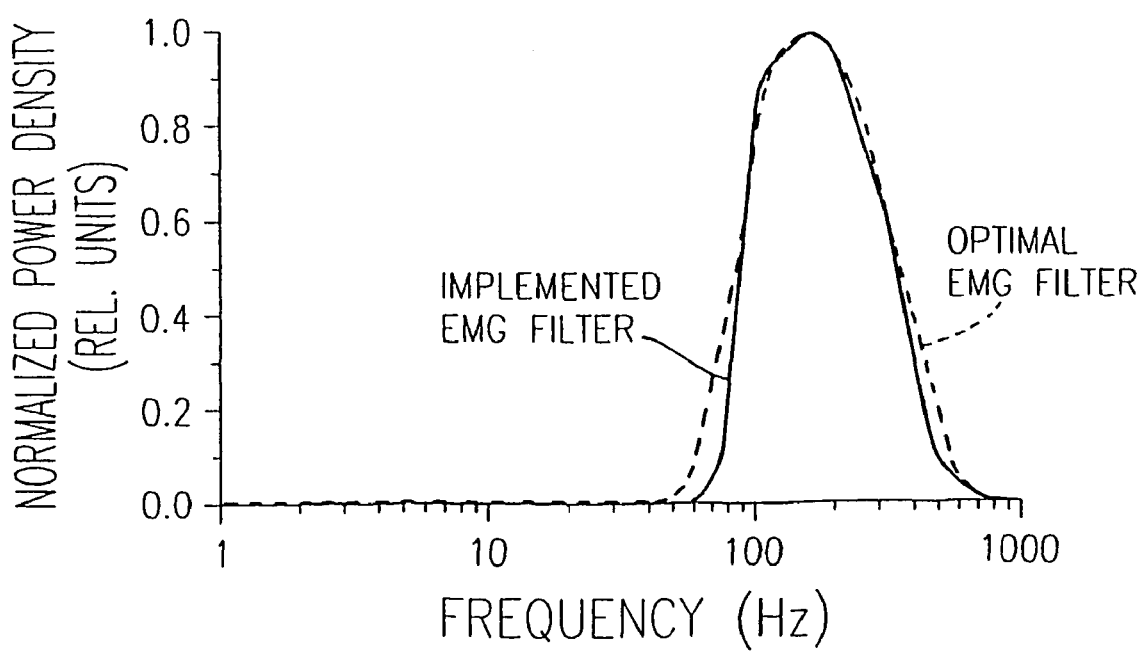
FIG. 10b is a graph showing an example of transfer function for a filter to be used for filtering out the electrode motion artefacts, electrocardiogram (ECG), the 50 or 60 Hz disturbances from electrical mains and high frequency noise.

FIG. 10b presents an optimal filter transfer function to isolate the EMGdi from a compound signal including ECG and also disturbed by background noise and electrode motion artefacts. In FIG. 10b, the dashed line shows the optimal transfer function, while the solid line shows the transfer function implemented by the inventors. FIG. 10b is therefore an example of filter transfer function that can be used in substep 202 for filtering out the electrode motion artefacts, ECG, the 50 or 60 Hz disturbance from the electrical mains, and the high frequency noise. Processing of the EMGdi signals by the computer 20 to follow, as closely as possible, the optimal transfer function of FIG. 10b will provide adequate filtering in substep 202.

An example of integrated EMGdi signal from a chronic obstructive pulmonary diseased (COPD) patient in relation to oesophageal and gastric pressure is depicted in FIGS. 10a and 10b.

Substep 204 involves the determination of the position of the centre of the DDR.

As the diaphragm is generally perpendicular to the longitudinal axis of the oesophageal catheter 16 equipped with an array of electrodes 22, only a portion of the electrodes 22 are situated in the vicinity of the diaphragm 24. Determining the position of the diaphragm 24 with respect to the oesophageal electrode array 12 therefore provides for better results.

The portion of the crural diaphragm 24, which forms the muscular tunnel through which the oesophageal catheter 16 is passed, is referred to the "diaphragm-depolarizing region" (DDR). The thickness of the DDR is about 20-30 mm. It is assumed that, within the DDR, the distribution of active muscle fibres has a centre from which the majority of the EMGdi signals originate, i.e. the "diaphragm-depolarizing region centre" (DDR centre). Therefore, EMGdi signals detected on opposite sides of the DDR centre will be reversed in polarity with no phase shift; i.e. EMGdi signals obtained along the electrode array 12 are reversing in polarity at the DDR centre.

Moving centrally from the boundaries of the DDR, EMGdi power spectrums progressively attenuate and enhance in frequency. Reversal of signal polarity on either side of the electrode pair 4 with the most attenuated power spectrum confirms the position from which the EMGdi signals originate, the DDR centre.

In step 204 of FIG. 9a, the position of the centre of the DDR along the array of electrodes 22 is determined.

The centre of the DDR is repeatedly updated, that is re-determined at predetermined time intervals. For that purpose, the EMGdi signals are cross-correlated in pairs in substep 204a to calculate cross-correlation coefficients r. As well known to those skilled in the art, cross-correlation is a statistical determination of the phase relationship between two signals and essentially calculates the similarity between two signals in terms of a correlation coefficient r. A negative correlation coefficient r indicates that the cross-correlated signals are of opposite polarities.

FIG. 12 shows curves of the value of the correlation coefficient r versus the midpoint between the pairs of electrodes 22 from which the correlated EMGdi signals originate. In this example, the inter-electrode distance d is 10 mm. Curves are drawn for distances between the correlated pairs of electrodes 22 of 5 mm (curve 52), 10 mm (curve 54), 15 mm (curve 56) and 20 mm (curve 58). One can appreciate from FIG. 12, that negative correlation coefficients r are obtained when EMGdi signals from respective electrode pairs situated on opposite sides of the electrode pair 4 are cross-correlated. It therefore appears that the change in polarity occurs in the region of electrode pair 4, which is confirmed by the curves of FIG. 4. Accordingly, it can be assumed that the centre of the DDR is situated substantially midway between the electrodes 22 forming pair 4.

In substep 204b, the correlation coefficients are systematically compared to determine the centre of the DDR. For example, the centre of the DDR can be precisely determined by interpolation using a square law based fit of the three most negative correlation coefficients of curve 54 from FIG. 12 obtained by successive cross-correlation of the EMGdi signal segments from each electrode pair to the EMGdi signal segments from the second next electrode pair. Association of the centre of the DDR to a pair of electrodes 22 provides a "reference position" from which to obtain EMGdi signal segments within the DDR.

As mentioned in the foregoing description, the position of the DDR centre along the array of electrodes 22 is continuously updated, i.e. re-calculated at predetermined time intervals overlapping or not. In substep 204c, update of the position of the DDR centre is controlled by comparing the most negative correlation coefficient $r_{NEG}$ to a constant K3 (substep 204d). If $r_{NEG}$<K3, it is considered that the EMGdi signal represents the diaphragm 24 and the position of the centre of the DDR is updated (substep 204e); if $r_{NEG}$>K3, it is considered that the EMGdi signal does not represent the diaphragm 21 and the position of the centre of the DDR is not updated (substep 204f). The control carried out in substep 204c allows overcoming the artefactual influence on the EMGdi power spectrum or signal strength measurement.

It has been experimentally demonstrated that EMGdi signals recorded in the oesophagus of adults are satisfactory as long as they are obtained from electrode pairs (with an inter-electrode distance situated between 5 and 20 mm) positioned at a distance situated between 5 and 30 mm on the opposite sides of the DDR centre (the inter-pair distance being therefore situated between 5 and 30 mm). With infants, this may change. Although EMGdi signals obtained from these positions offer a clear improvement in acceptance rates, the signal-to-noise ratio during quiet breathing still tends to remain unsatisfactorily low.

Figure 13:
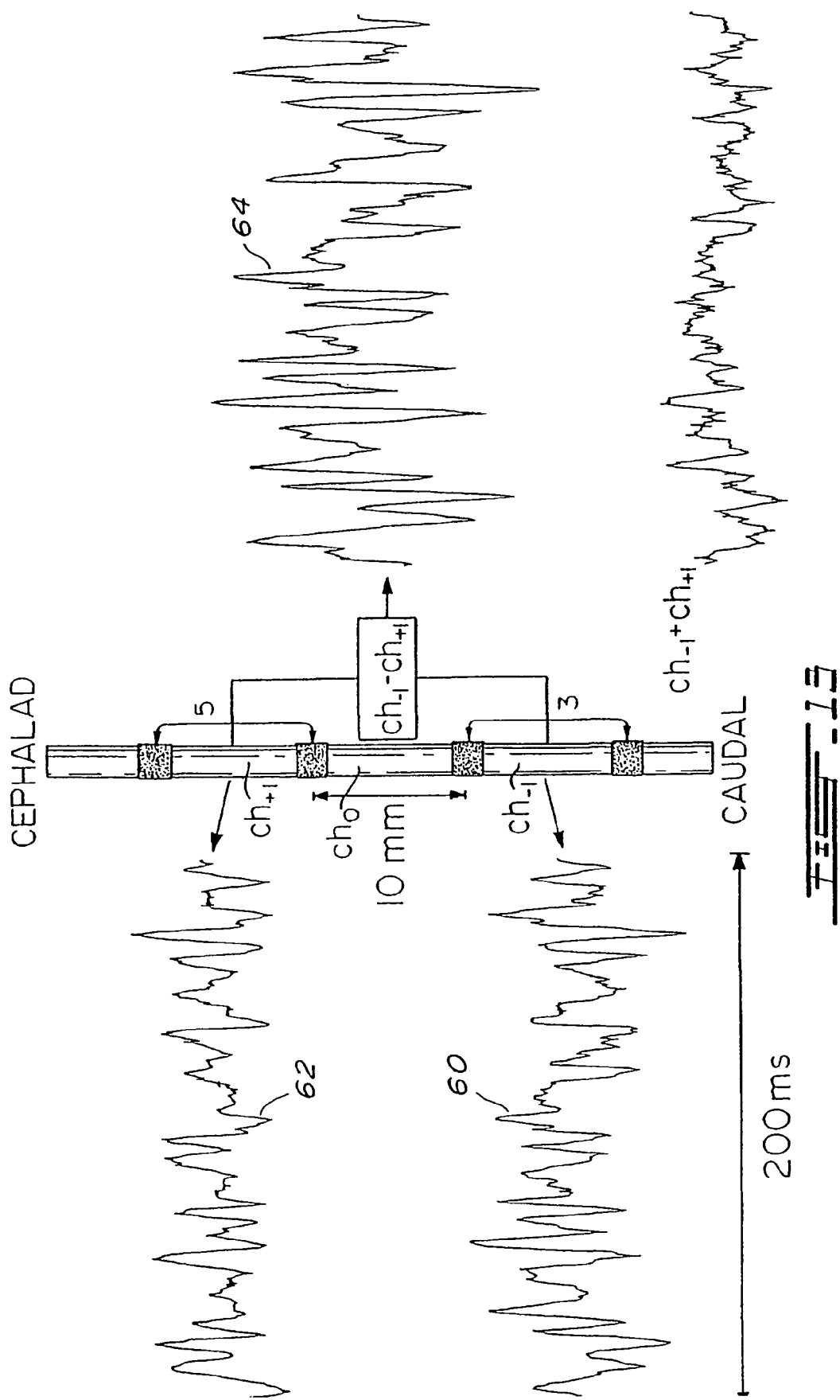
FIG. 13 is a schematic view with graphs illustrating, in the time domain, a double subtraction technique for improving the signal-to-noise ratio and to reduce an electrode-position-induced filter effect.

For example, in FIG. 4, the EMGdi signals originating from the electrode pairs 3 and 5, situated respectively 10 mm below and 10 mm above the DDR, are strongly inversely correlated at zero time delay. In contrast to the inversely correlated EMGdi signals, the noise components for electrode pairs 3 and 5 are likely to be positively correlated. Hence, as illustrated in FIG. 13, subtraction of the EMGdi signals 60 and 62 from electrode pairs 3 and 5 will result in an addition of the corresponding EMGdi signals (see signal 64) and in a subtraction, that is, an elimination of the common noise components. This technique is referred to as "the double subtraction technique".

This second subtraction step of the double subtraction technique can be carried out either in the time domain, or after conversion of signals 60 and 62 into the frequency domain. A double subtraction technique can be performed by subtracting other combinations of signals, or by altering the polarities of electrode pairs. Two signals of opposite polarities obtained in the vicinity of the muscle on opposite sides of the DDR are subtracted, or if polarity is altered, on opposite sides of the DDR, to add signals from opposite sides of the DDR.

Therefore, double-subtracted signal segments 206 are obtained at the output of step 206a by subtracting the EMGdi signal segments from the pair of electrodes 22 in optimal location above the diaphragm 24 from the EMGdi signal segments from the pair of electrodes 22 in optimal location below the diaphragm 24.

The double subtraction technique compensates for the changes in signal strength and frequency caused by movement of the diaphragm 24 (FIG. 1) and/or the oesophagus during breathing of the patient 26 causing movement of the array of electrodes 22 with respect to the diaphragm 24.

Figure 14:
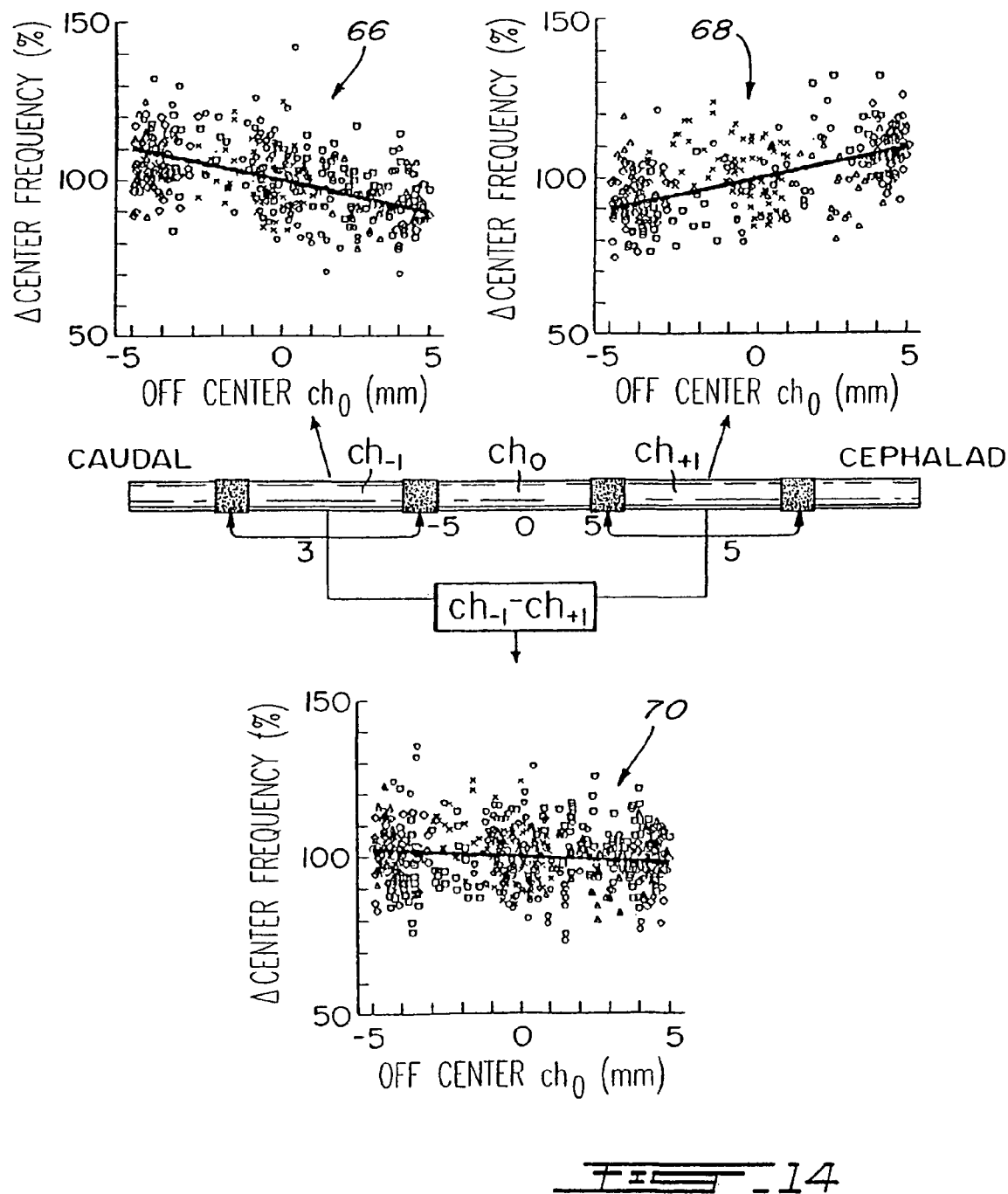
FIG. 14 is a schematic diagram, illustrating in the frequency domain, stabilization by the double subtraction technique of the centre frequency upon displacement of the centre of the depolarizing region of the diaphragm of FIG. 1 along the array of electrodes of FIG. 2.
Figure 15A:
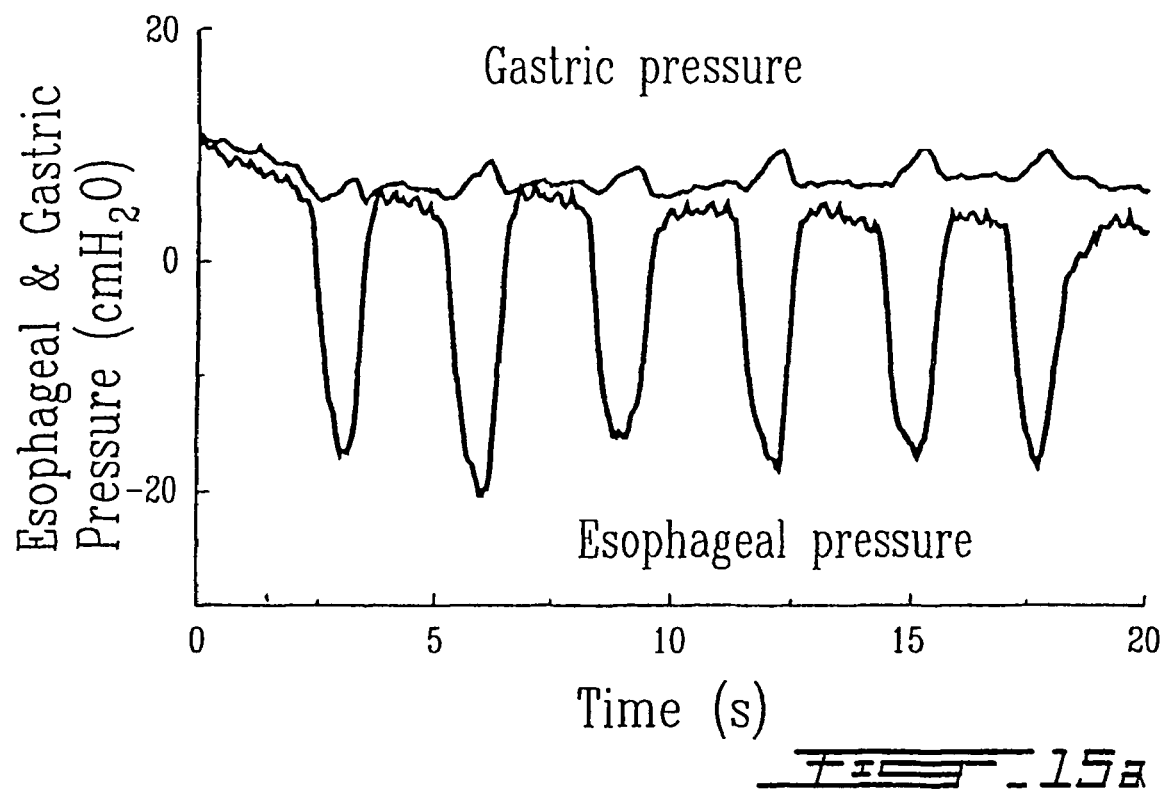
FIG. 15a is a graph of oesophageal and gastric pressure versus time for quiet breathing of a chronic obstructive pulmonary disease (COPD) patient.
Figure 15B:
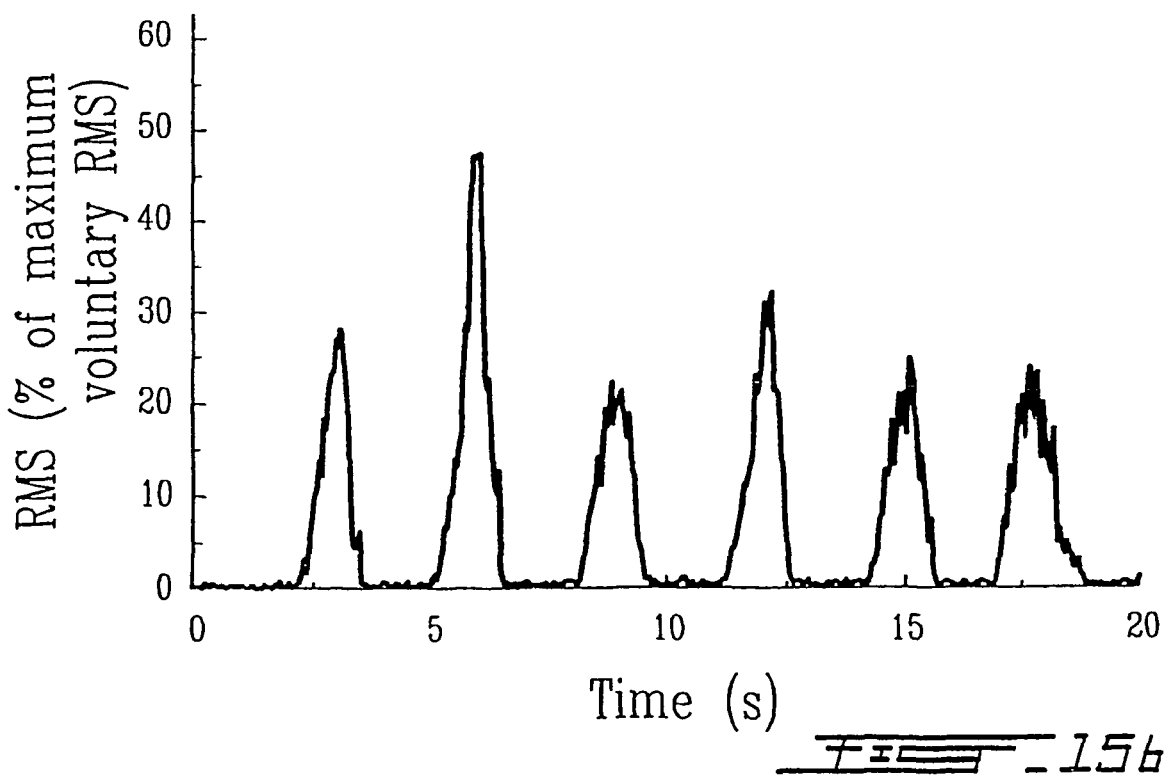
FIG. 15b is a graph of the RMS value of EMG versus time for quiet breathing of a COPD patient; the graphs of FIGS. 15a and 15b show the relation between EMG and the oesophageal and gastric pressure.

Referring to FIG. 14, off centre of the array of electrodes 22 (electrode-position-induced filter effect) causes a variation of centre frequency values (see curves 66 and 68) for the EMGdi signals from the electrode pairs 3 and 5. The double subtraction technique eliminates such variation of centre frequency values as indicated by curve 70 as well as variation of signal strength. Therefore, the reciprocal influence of the position of the DDR centre on the EMGdi signal frequency content is eliminated by the double subtraction technique.

It has been found that the double subtraction technique may improve the signal-to-noise ratio by more than 2 dB and reduce an electrode-position-induced filter effect. Double subtraction technique also allows for a relative increase in acceptance rates by more than 50%.

Cross-talk signals from adjacent muscles are strongly correlated at zero time delay and equal in polarity between all pairs of electrodes 22. Hence, these cross-talk signals appear as a common mode signal for all electrode pairs and therefore, are eliminated by the double subtraction technique.

In substep 206, the strength of the EMGdi signal is calculated. In substep 206a, a pair of EMGdi signals (signals 1-7 of FIG. 4) obtained from electrode pairs above and below the DDR centre are subtracted from each other and the RMS (Root-Mean-Square) value of the resulting signal is calculated and referred to as RMSsub (substep 206c). Measures of signal intensity, other than the RMS value, can also alternatively be used.

In a substep 206b, the above mentioned pair of EMGdi signals (see signals 1-7 of FIG. 4), obtained from electrode pairs above and below the DDR centre, are added to each other and the RMS (Root-Mean-Square) value of the resulting addition signal is calculated and referred to as RMSadd (substep 206d). Measures of signal intensity other than the RMS value can also potentially be used.

In substep 208, a sufficient increment of the RMS signal amplitude RMSsub is detected. More specifically, in substep 208a, the RMS amplitude RMSsubn of the last EMGdi subtraction signal segment, as calculated by substep 206c, is compared with the RMSsubn−1 of EMGdi subtraction signal segment last accepted in substep 210c. If (RMSsubn× K1)<RMSsubn−1, no increment is detected and the system will wait until analysis of the next EMGdi subtraction signal segment is performed. On the contrary, if (RMSsubn× K1)>RMSsubn−1, an increment of the RMS intensity of the EMGdi signal is detected and detection of the common mode influence (substep 210) is activated. Of course, the multiplication operation (×K1) can be replaced by other suitable mathematical operations conducted on either the term RMSsubn or RMSsubn−1.

Substep 210 enables detection of signal artefacts of non-diaphragmatic origin. As indicated in the foregoing description, EMGdi signals generated by the diaphragm and recorded on either side of the diaphragm 24 will have reversed polarity and no time delay. Accordingly, a subtraction signal, representative of the difference between these two EMGdi signals, will have a larger amplitude than an addition signal representing the sum of such EMGdi signals. In contrast, signals generated away from, and on the same side of the diaphragm 24, will have the same polarity on all electrode pairs and no time delay. As well, signals from the heart that are not obtained with electrode pairs located too far apart will have a similar shape but will have a time delay. Differing from signals with reversed polarity, subtracted signals with the same polarity will have smaller amplitudes than added signals. Hence the ratio or difference between the sum and difference between signals obtained from the same electrode pairs on either side of the diaphragm can indicate if a signal is of a diaphragm or an artefactual origin.

For that purpose, in substep 210b, the amplitude RMSsubn is compared with the amplitude RMSaddn multiplied by a constant K2. It is to be noted that the indicia "n" is representative of the last EMGdi subtraction or addition signal segment. If RMSsubn<(RMSaddn×K2), the RMS signal amplitude is rejected (substep 210a) and the two EMGdi signals are considered to have an artefactual origin. If RMSsubn>(RMSaddn×K2), the RMS signal amplitude is accepted (substep 210c) and the two EMGdi signals are considered to have a diaphragm origin. Of course, the multiplication operation (×K2) can be replaced by other suitable mathematical operations conducted on either the term RMSsubn or RMSaddn.

In EMGdi signal replacement substep 216, a substep 216a determines whether the last RMS signal amplitude is accepted. If the last RMS signal amplitude is accepted, RMSsubn is kept (substep 216a). If the last RMS signal amplitude is not accepted, RMSsubn is replaced by RMSsubn−1 or with another prediction (substep 216c).

An increase in amplitude of RMSsubn does not necessarily mean that the diaphragm 24 is the signal source. It is therefore advantageous to discriminate signals originating from the diaphragm 24 from signals of other origins. In the foregoing description, it has been described that a technique of sequential cross-correlation of the EMGdi signals from pairs of electrodes 22 can be used to determine the location of the diaphragm by the most negative correlation coefficient rNEG. Other simplified calculations of correlation can be used. The magnitude of the correlation coefficient rNEG is characteristic of each subject but is typically negative when the diaphragm is active. If the diaphragm is not active, the negative correlation coefficient rNEG is very low or the correlation coefficient is positive. The onset of diaphragm activation can therefore be detected through the amplitude of the correlation coefficient rNEG.

To determine the mean level of noise RMSsubNOISE (step 218), a mean amplitude of RMSsubn is calculated. For that purpose, when rNEG>K4, K4 being a constant, this indicates that the diaphragm is not active (substep 218a) and the mean level of RMSsubn, i.e. RMSsubNOISE is calculated (substep 218b) and outputted. If rNEG<K4, the system 10 remains in an idle state (step 218c).

An alternative to substep 218 is to detect the onset of inspiration through detection of airway inspiratory flow.

Even though step 102 has been described by referring to the measurement of the myoelectrical activity of the diaphragm 24 using the system 10, the measurement of other respiratory-related EMG can be obtained with a suitable device placed in the vicinity of the respiratory-related muscle, inserted or implanted on the surface of or into the muscle of interest.

Furthermore, other increases in EMGdi signal amplitude, its integrals or derivatives or combinations thereof, detected via an EMG recording of the diaphragm or other muscles associated with inspiration above a desired threshold level, and exceeding a desired duration, can be used to indicate the onset of an inspiratory effort.

The magnitude of the signal itself may also be used. The signal can be applied, for example, in proportion to the signal times a constant and its maximum value up to a certain pressure or volume level.

After a myoelectrical signal representative of the inspiratory effort of the patient 26 has been obtained, this signal is compared, in step 104, to a predetermined threshold so as to determine the highest value therebetween, and to send a control command to the respiratory sealing device 18 so as to modify the state of the sealing device according to a comparison result (step 106).

Determination of the level to be exceeded (threshold) in terms of amplitude and duration can either be performed by manual adjustment supervised via visual feedback, or by automatically letting the level be relative to the above described mean noise level. An algorithm can further be used to trigger the respiratory sealing device 18 when the amplitude of an EMG signal segment of defined duration exceeds the threshold.

The duration of time that the EMG amplitude remains above the threshold level can be used to decide the duration of the breath e.g. the ventilatory support system can start and deliver a full breath independent of the presence of EMG activity that exceeds the threshold level. The algorithm can also be adjusted to discontinue the ventilatory support if the EMG amplitude drops below the threshold level, or in response to a decrease in amplitude that exceeds a given magnitude (decrement).

In step 104, the RMS amplitude RMSsubn may be compared to a predetermined parameter P5.

If RMSsubn>P5, the RMS amplitude is higher than the threshold P5 and the sealing device 18 is activated so as to seal the air leak to avoid gas leaks during the respiratory effort of the patient 26.

If, on the other hand, RMSsubn<P5 the RMS amplitude is below the threshold P5, and the sealing device 18 is activated so as to unseal the air leak to allow gas leaks during the relaxation of the patient's respiratory effort. P5 is a parameter equal to $RMSsub_{NOISE} \times K7$, K7 being a predetermined constant. It is to be noted that the parameter P5 would normally be different for triggering on and triggering off the sealing device 18 since the noise level is different in both cases.

Again, the multiplication operation (×K7) can be replaced by other suitable mathematical operations conducted on term $RMSsub_{NOISE}$.

Alternatively or additionally to the comparison between the myoelectrical signal corrected amplitude RMSsub to a predetermined threshold, a RMSsub amplitude increment and decrement detection can be performed. The predetermined value to which the amplitude is compared is, in this particular case, a prior measured and corrected signal amplitude.

The prior value RMSsubn−1 is compared to (RMSsubn× K6). If (RMSsubn×K6)<RMSsubn−1, the sealing device 18 remains in an idle state. If (RMSsubn×K6)>RMSsubn−1, this indicates an increment of the RMS amplitude, and sealing of the air leak by the sealing device 18 is requested through an increment counting/integrating to support the patient 26. The multiplication operation (×K6) can be replaced by other suitable mathematical operations conducted on either the term RMSsubn or RMSsubn−1.

The function of the increment counting/integrating substep is to determine the time/magnitude response. The increment signal is averaged to adjust to sensitivity.

The prior value RMSsubn−1 is also compared to (RMSsubn×(1/K6)). If (RMSsubn×(1/K6))>RMSsubn−1, the sealing device 18 remains in an idle state. If (RMSsubn× (1/K6))<RMSsubn−1, this indicates a decrement of the RMS amplitude and unsealing of the air leak is performed via the sealing device 18 through a decrement counting/integrating step. Of course, the multiplication operation (×(1/K6)) can be replaced by other suitable mathematical operations conducted on either the term RMSsubn or RMSsubn−1.

The function of the decrement counting/integrating step is to determine the time/magnitude response. The decrement signal is averaged to adjust to sensitivity.

In response to EMG signals, airway inspiratory flow and/or pressure control commands are sent by the computer 20 for triggering a ventilatory support system (ventilator) through an interface (not shown). Indeed, the system 10 advantageously comprises a digital-to-analog converter and/or other means for analog and digital interface.

The decision for triggering will be made by a logic circuit on a "first come, first serve" basis. For example, if the diaphragm EMG (or EMG of other inspiratory related muscle) indicates an inspiratory effort before airway inspiratory flow and/or pressure indicates the onset of inspiration, the ventilatory support will be engaged. In the same fashion, the ventilatory support will be initiated if the inspiratory effort is detected by a threshold for airway inspiratory flow and/or pressure being exceeded before the EMG threshold is exceeded.

Other changes in airway inspiratory flow and/or pressure, its integrals or derivatives or combinations thereof, in the inspiratory direction beyond a desired threshold level and detected via the inspiratory and/or expiratory lines can be used to indicate the onset of an inspiration.

Figure 11A:
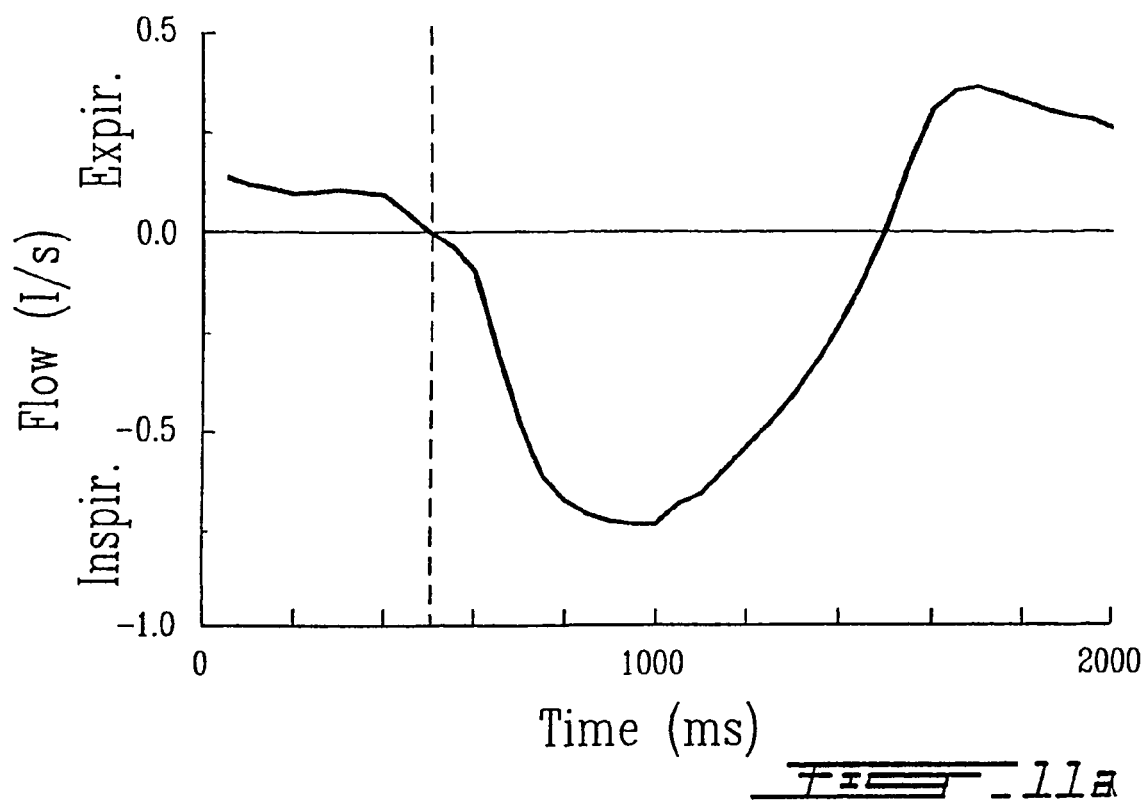
FIG. 11a is a graph of inspiratory and expiratory flow versus time for quiet breathing of a chronic obstructive pulmonary disease (COPD) patient.
Figure 11B:
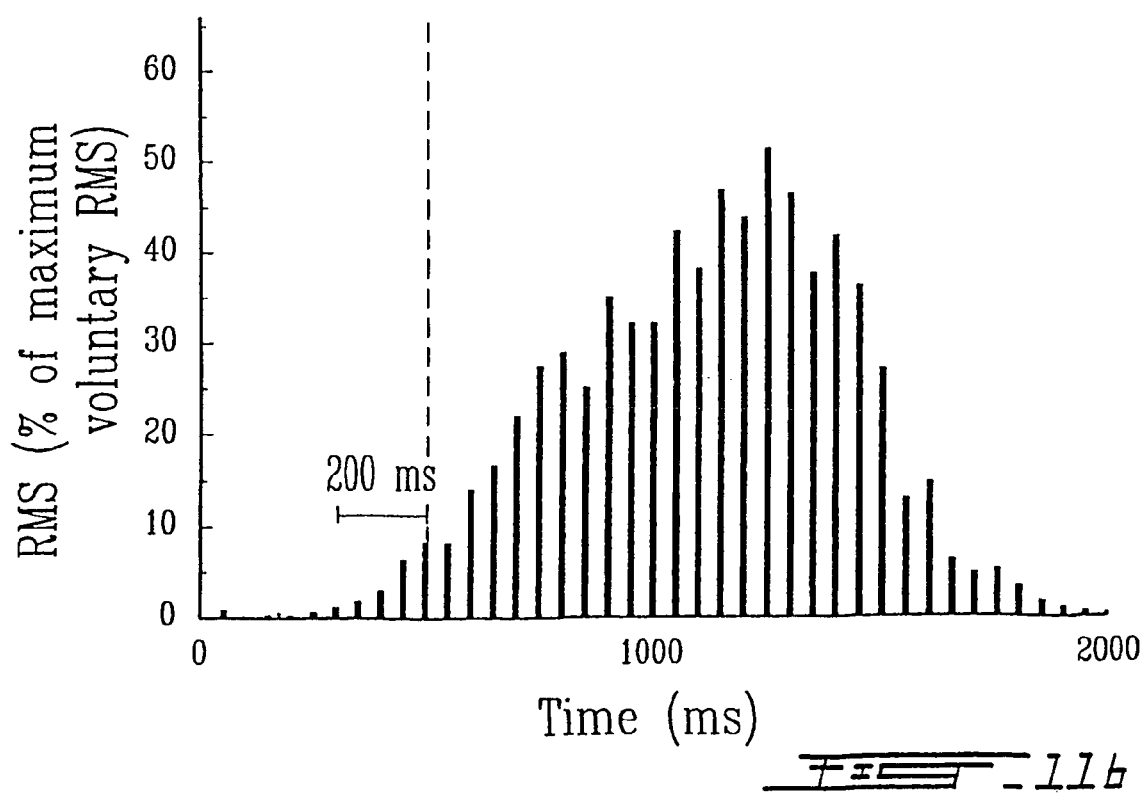
FIG. 11b is a graph of the RMS value of EMG versus time for quiet breathing of a COPD patient, the graphs of FIGS. 10a and 10b showing the time delay from EMG to airway inspiratory flow.

The graphs in FIGS. 10*a* and 10*b* show, in the case of the quiet breathing of a COPD patient, that an EMG RMS signal will be detected approximately 200 ms prior to the onset of airway inspiratory flow. The graphs in FIGS. 11*a* and 11*b* show, still in the case of the quiet breathing of a COPD patient, a similar relation between EMG RMS signal and the gastric and oesophageal pressure. In this particular example, sealing/unsealing in response to an EMG will enable the airleak regulating device to assist the patient directly at the onset of inspiration occurring 200 ms after detection of an EMG RMS amplitude signal.

The method and device according to the invention is applicable to all patients (adults and infants) on ventilatory support and can enhance the possibilities of obtaining spontaneous breathing and optimizing patient ventilator interaction. The method and device applies to many kinds of ventilatory support systems used in intensive care unit settings and other wards where assisted ventilation is applied, and to other respiratory sealing devices (also referred to as an air leak regulating device).

It is to be noted that substeps 204 and 210 of FIG. 9 are part of the double subtraction technique and are therefore not necessarily executed with other signal analysis techniques. Moreover, substep 210 is optional even when using the double subtraction technique.

Alternatively, the operation of a system according to the present invention can be based on the amplitude of the signals or the area under the curve (integration) of these signals, or other measures of signal strength.

Although the preferred embodiment of the present invention will be described in relation to the use of an EMGdi signal obtained by means of a double subtracted signal, and representative of the myoelectrical activity of the diaphragm, it should be kept in mind that it is within the scope of the present invention to use another type of EMGdi signal, or to use a signal representative of the myoelectrical activity of muscles other than the diaphragm, yet associated with inspiratory effort to trigger the ventilatory support apparatus. Examples of other muscles are parasternal intercostal muscles, sternocleidomatoids, scalenes, alae nasi, etc. The myoelectrical activity of these muscles can eventually be detected by means of electrodes directly implanted in the muscle.

Although the present invention has been described hereinabove by way of preferred embodiments thereof, it can be modified without departing from the spirit and nature of the subject invention, as defined in the appended claims.

What is claimed is:

1. A method for controlling an air seal between a ventilator air circuit and a patient's respiratory airways, comprising:
    mounting an air seal modifier between the ventilator air circuit and the patient's respiratory airways;
    sensing myoelectrical activity of a respiratory-related muscle of the patient to produce a myoelectrical signal representative of respiratory effort of the patient;
    analyzing the myoelectrical signal to produce an air seal controlling signal; and
    controlling the air seal modifier in response to the air seal controlling signal to (a) seal the air seal between the ventilator air circuit and the patient's respiratory airways during respiratory effort of the patient, and (b) unseal the air seal between the ventilator air circuit and the patient's respiratory airways to allow gas leaks during relaxation of respiratory effort of the patient.

2. A method for controlling an air seal as recited in claim 1, wherein the respiratory-related muscle is selected from the group consisting of diaphragm, parasternal intercostal muscles, sternocleidomatoids, scalenes, and alas nasi.

3. A method for controlling an air seal as recited in claim 2, wherein the respiratory-related muscle is the diaphragm.

4. A method for controlling an air seal as recited in claim 3, wherein the myoelectrical activity is sensed in an electrically active region of the diaphragm (DDR).

5. A method for controlling an air seal as recited in claim 4, wherein the myoelectrical activity is sensed near a centre of the DDR.

6. A method for controlling an air seal as recited in claim 5, wherein sensing the myoelectrical activity of the respiratory-related muscle comprises sensing at least one signal above said DDR and at least one signal below said DDR, and subtracting these two signals to yield at least one myoelectrical signal representative of the respiratory effort of the patient.

7. A method for controlling an air seal as recited in claim 1, wherein:
    the sensing the myoelectrical activity of the respiratory-related muscle of the patient step comprises producing at least one myoelectrical signal representative of respiratory effort of the patient;
    the analyzing the myoelectrical signal step comprises comparing the myoelectrical signal to a predetermined value so as to determine a highest value between a value of the myoelectrical signal and the predetermined value, wherein the highest value forms the air seal controlling signal; and
    the controlling the air seal modifier step comprises controlling the air seal modifier in response to the highest value.

8. A method for controlling an air seal as recited in claim 7, further comprising filtering from said at least one myoelectrical signal at least one of the following disturbances: motion artifacts, electrocardiogram (EGG), electrical interference, and high frequency noise.

9. A method for controlling an air seal as recited in claim 7, wherein the predetermined value is a predetermined threshold, and wherein controlling the air seal modifier comprises (a) sealing the air seal between the ventilator air circuit and the patient's respiratory airways when said at least one myoelectrical signal is the highest value, thereby avoiding gas leaks during respiratory effort of the patient, and (b) unsealing the air seal between the ventilator air circuit and the patient's respiratory airways when the predetermined threshold is the highest value, thereby allowing gas leaks during relaxation of the respiratory effort of the patient.

10. A method for controlling an air seal as recited in claim 9, wherein two different thresholds are used in (a) and in (b).

11. A method for controlling an air seal as recited in claim 9, wherein the predetermined threshold is predetermined by manual adjustment using visual feedback.

12. A method for controlling an air seal as recited in claim 9, wherein the predetermined threshold is predetermined automatically by letting the level be relative to a predetermined noise level.

13. A method for controlling an air seal as recited in claim 7, wherein the analyzing the myoelectrical signal step further comprises multiplying a current sample of said at least one myoelectrical signal by a predetermined constant to produce a multiplied sample; wherein the predetermined value corresponds to a prior sample of said at least one myoelectrical signal; and wherein the controlling the air seal modifier step comprises (a) sealing the air seal between the ventilator air circuit and the patient's respiratory airways when a value of the multiplied sample is the highest value, thereby avoiding gas leaks during the respiratory effort of the patient, and (b) unsealing the air seal between the ventilator air circuit and the patient's respiratory airways when a value of the prior sample of said at least one myoelectrical signal is the highest value, thereby allowing gas leaks during relaxation of the respiratory effort of the patient.

14. A method for controlling an air seal as recited in claim 7, further comprising detecting a level of noise in said at least one myoelectrical signal; and determining whether the respiratory-related muscle of the patient is active in relation to the detected level of noise.

15. A system for controlling an air seal between a ventilator air circuit and a patient's respiratory airways, comprising:
    a modifier of the air seal;
    a sensor of a myoelectrical activity of a respiratory-related muscle of the patient to produce a myoelectrical signal representative of respiratory effort of the patient;
    an analyzer of the myoelectrical signal to produce an air seal controlling signal; and
    an air seal controller responsive to the air seal controlling signal to activate the air seal modifier for (a) sealing the air seal between the ventilator air circuit and the patient's respiratory airways during respiratory effort of the patient, and (b) unsealing the air seal between the ventilator air circuit and the patient's respiratory airways to allow gas leaks during relaxation of the respiratory effort of the patient.

16. A system for controlling an air seal as recited in claim 15, wherein the air seal modifier comprises a sealing balloon.

17. A system for controlling an air seal as recited in claim 16, wherein:
    the sealing balloon is mounted on a ventilatory assist tube of the ventilator air circuit; and
    the ventilatory assist tube includes a first lumen defining an air passage of the ventilator air circuit, and a second lumen defining a fluid passage for fluid communication between the sealing balloon and a balloon inflation device and pressure control of the sealing balloon both forming part of the air seal controller.

18. A system for controlling an air seal as recited in claim 15, wherein the air seal modifier comprises a face mask including a seal pressure lumen.

19. A system for controlling an air seal as recited in claim 15, wherein the sensor comprises an array of electrodes.

20. A system for controlling an air seal as recited in claim 19, wherein the array of electrodes is provided with a constant inter-electrode distance.

21. A system for controlling an air seal as recited in claim 19, wherein the array of electrodes includes nine electrodes.

22. A system for controlling an air seal as recited in claim 19, further comprising at least one differential amplifier connected to both the electrodes and the analyzer.

23. A system for controlling an air seal as recited in claim 22, wherein said at least one differential amplifier includes single-ended amplifiers, allowing monopolar readings.

24. A system for controlling an air seal as recited in claim 22, wherein said at least one differential amplifier is connected to the electrodes via electric wires.

25. A system for controlling an air seal as recited in claim 24, further comprising means for filtering from the myoelectrical signal at least one of the following disturbances: motion artifacts; EGG, electrical interference, and high frequency noise.

26. A system for controlling an air seal as recited in claim 22, wherein the array of electrodes comprises pairs of electrodes and wherein said at least one differential amplifier comprises a differential amplifier for each pair of electrodes.

27. A system for controlling an air seal as recited in claim 22, wherein said at least one differential amplifier is configured for sampling the myoelectrical signal to form signal segments.

28. A system for controlling an air seal as recited in claim 15, wherein the sensor is mounted on a free end of a catheter.

29. A system for controlling an air seal as recited in claim 28, wherein the sensor includes a steel wire wound around the catheter.

30. A system for controlling an air seal as recited in claim 29, wherein the steel wire wound around the catheter is smoothed out by solder.

31. A system for controlling an air seal as recited in claim 28, wherein the catheter is an oesophageal catheter.

32. A system for controlling an air seal as recited in claim 15, wherein the sensor is mounted on a free end of a nasogastric tube.

33. A system for controlling an air seal as recited in claim 15, wherein the analyzer comprises a personal computer.

34. A system for controlling an air seal as recited in claim 15, wherein the analyzer comprises a comparator of the myoelectrical signal with a predetermined value to produce the air seal controlling signal.

35. A system for controlling an air seal between a ventilator air circuit and a patient's respiratory airways, comprising:
    means for modifying the air seal;
    means for sensing myoelectrical activity of a respiratory related muscle of the patient to produce a myoelectrical signal representative of respiratory effort of the patient;
    means for analyzing the myoelectrical signal to produce an air seal controlling signal; and
    air seal control means responsive to the air seal controlling signal to activate the air seal modifying means for (a) sealing the air seal between the ventilator air circuit and the patient's respiratory airways during respiratory effort of the patient, and (b) unsealing the air seal between the ventilator air circuit and the patient's respiratory airways to allow gas leaks during relaxation of respiratory effort of the patient.

\* \* \* \* \*